(12) United States Patent
Begemann

(10) Patent No.: US 6,694,189 B2
(45) Date of Patent: Feb. 17, 2004

(54) RATE ADAPTIVE PACEMAKER SYSTEM WITH DUAL SENSING COMPONENT AND METHOD OF USING SAME

(75) Inventor: Malcolm Begemann, Velp (NL)

(73) Assignee: Medtronic, Inc., Minneapolis, MN (US)

( * ) Notice: Subject to any disclaimer, the term of this patent is extended or adjusted under 35 U.S.C. 154(b) by 360 days.

(21) Appl. No.: 09/799,708

(22) Filed: Mar. 7, 2001

(65) Prior Publication Data

US 2002/0161411 A1 Oct. 31, 2002

(51) Int. Cl.$^7$ ............................................... A61N 1/365
(52) U.S. Cl. ............................................ 607/18; 607/25
(58) Field of Search .................................. 607/17–26

(56) References Cited

U.S. PATENT DOCUMENTS

| 4,712,555 | A | * | 12/1987 | Thornander et al. ........... 607/17 |
| 4,856,524 | A |   | 8/1989  | Baker, Jr. |
| 5,144,950 | A |   | 9/1992  | Stoop et al. |
| 5,741,308 | A | * | 4/1998  | Sholder ......................... 607/9 |
| 6,122,546 | A | * | 9/2000  | Sholder et al. ................ 607/9 |

* cited by examiner

Primary Examiner—Jeffrey R. Jastrzab

(57) ABSTRACT

A method and system of adapting heart rate in cardiac tissue based on two types of sensed information is provided. A pulse is transmitted to the cardiac tissue. An activity signal is received. A first interval signal is also received and the pacing rate is adapted based on the first interval signal. A second interval signal is then received and the adapted pacing rate is verified using the second interval signal.

15 Claims, 9 Drawing Sheets

RATE ADAPTIVE PACEMAKER SYSTEM WITH DUAL SENSING COMPONENT AND METHOD OF USING SAME

FIELD OF THE INVENTION

The present invention relates to the field of implantable medical devices, and, more particularly, to cardiac pacing systems that adapt the pacing rate by using two types of sensed information, for example from two different sensors, to determine the required heart rate and to adjust the pacing rate appropriately.

BACKGROUND OF THE INVENTION

Implantable pulse generators (or IPGs) are well known in the art. Some of these devices provide pacing stimuli to the heart at a predetermined rate. The stimuli may be applied at a fixed rate, on demand, at a rate synchronized to atrial activity or at a rate synchronized to ventricular activity. This type of pacing function may also be used in other devices such as, for example, implantable cardioverter defibrillators (ICDs) or in external pacemakers. Most IPGs include sense amplifier circuitry for detecting intrinsic cardiac electrical activity. Some IPGs also include sensors to determine reliably the heart rate (or pacing rate) in a heart under different conditions.

This may occur, for example, when a sensor indicates a heart workload that is too high (a false positive). For example, a sensor may indicate high cardiac workload in a person when, in fact, the person is only sitting on a bus on a bumpy road, attending a particularly raucous concert or in another such shaky environment. On some occasions, brushing one's teeth may induce movements in the upper body that may be inappropriately sensed as a high cardiac workload.

With a heart rate that is artificially increased to an inappropriately high rate, the conduction time to the ventricle may be prolonged. Although this is a normal electrophysiological phenomenon, it is of some concern that the conduction time may be overly prolonged, even to a level where conduction to the ventricle is blocked. Thus, it would be desirable to determine an appropriate rate of stimulation for any given conditions, e.g., the number of times per specific period that a stimulating pulse should be delivered for the desired response to be evoked under the given set of conditions. In particular, a rate of stimulation that produces a more physiological heart rate with a suitable conduction time to the ventricle would be desirable. Such a rate of stimulation would protect the heart from too prolonged a conduction time to the ventricle, and would help prevent blockage of conduction to the ventricle.

Thus, a need exists in the medical arts for evaluating the rate of activity at which a pacing pulse is administered and adjusting the rate if necessary.

Several methods have been proposed in the prior art for improving an implantable device's ability to administer pacing pulses.

For example, U.S. Pat. No. 5,144,950 to Stoop et al., entitled "Rate Controlled Pacemaker System Using AR Interval for Rate Control", hereby incorporated by reference in its entirety, discloses an AAIR rate responsive device that uses the measured A-R interval to control the rate response.

U.S. Pat. No. 4,856,524 to Baker, entitled "A-V Responsive Rate Adaptive Pacemaker" hereby incorporated by reference in its entirety, discloses an A-V responsive IPG where the pacing interval is based on one of two linear functions depending upon whether atrial activity is spontaneous or induced.

As discussed above, the most pertinent prior art patents are shown in the following table:

TABLE 1

| Prior Art Patents. | | |
| --- | --- | --- |
| U.S. Pat. No. | Date | Inventor(s) |
| U.S. Pat. No. 5,144,950 | Sep. 8, 1992 | Stoop et al. |
| U.S. Pat. No. 4,856,524 | Aug. 15, 1989 | Baker, Jr. |

All the patents listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for adapting the rate in a cardiac pacing system by using two different types of sensed information, for example, from two sensors, to determine the required heart rate and to adjust the pacing rate appropriately. Such a system of the present invention overcomes the problems, disadvantages and limitations of the prior art described above, and provides a more efficient and accurate means of determining the heart rate and adjusting the pacing rate appropriately.

The present invention has certain objects. That is, various embodiments of the present invention provide solutions to one or more problems existing in the prior art respecting the instantaneous stimulation of a mammalian heart. Those problems include, without limitation: the ability to adapt the rate of stimulation appropriately based on the activity of the heart.

In comparison to known techniques for adapting the rate of stimulation, various embodiments of the present invention may provide the following advantage, inter alia, i.e., the ability to adapt the rate of stimulation by using two types of sensed information, for example information from two sensors, to determine the required heart rate and to adjust the pacing rate appropriately based on the sensed information.

Some of the embodiments of the present invention include one or more of the following features: an implantable medical device including at least one sensing lead capable of sensing two types of sensed data or including two sensing leads, at least one pacing lead, a microprocessor and an input/output circuit including a digital controller/timer circuit, an output circuit, a sense amplifier, a peak sense and threshold measurement device, a comparator, an electrogram amplifier, a sensor for determining basic rate response and an additional sensor for measuring the electrical conduction time to the ventricle, for example by measuring the time from a sensed atrial signal to a sensed ventricular signal (PR interval) or by measuring the time from an atrial pacing pulse to a ventricular sensed signal (AR interval).

Furthermore, in accordance with the present invention, an embodiment for a method and system of adapting heart rate in cardiac tissue based on two types of sensed information, where one type is the electrical conduction time to the ventricle, is provided. A pulse is transmitted to the cardiac tissue. An activity signal is received. A first interval signal is also received and the pacing rate is adapted based on the first interval signal. A second interval signal is then received and the adapted pacing rate is verified using the second interval signal.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

The term "atrial response" appearing herein may indicate a portion of an atrial sensed response, an entire atrial sensed response, a portion of an atrial pulse signal or an entire atrial pulse signal. The term "atrial signal" appearing herein may indicate a portion of an atrial sensed response, an entire atrial sensed response, a portion of an atrial pulse signal or an entire atrial pulse signal. The term "ventricular response" appearing herein may indicate a portion of a ventricular sensed response or an entire ventricular sensed response. The term "ventricular signal" appearing herein may indicate a portion of a ventricular signal or an entire ventricular signal.

Figure 1:
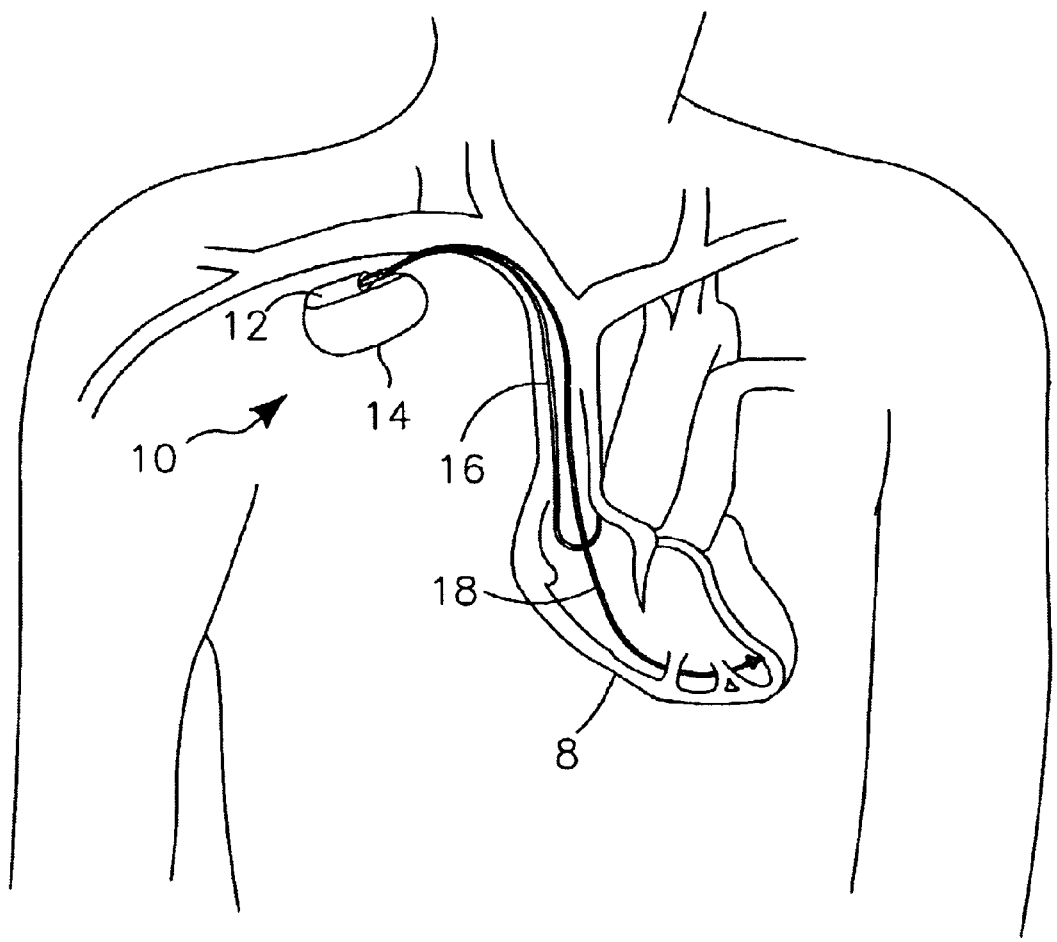
FIG. 1 is a schematic view of one embodiment of an implantable medical device in situ, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Sensing leads 16, 18 may serve, for example, as sensors to sense an atrial response (such as an atrial sensed response or an atrial pulse signal) in accordance with the present invention. One or both of leads 16,18 may also serve to sense a ventricular response in accordance with the present invention. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
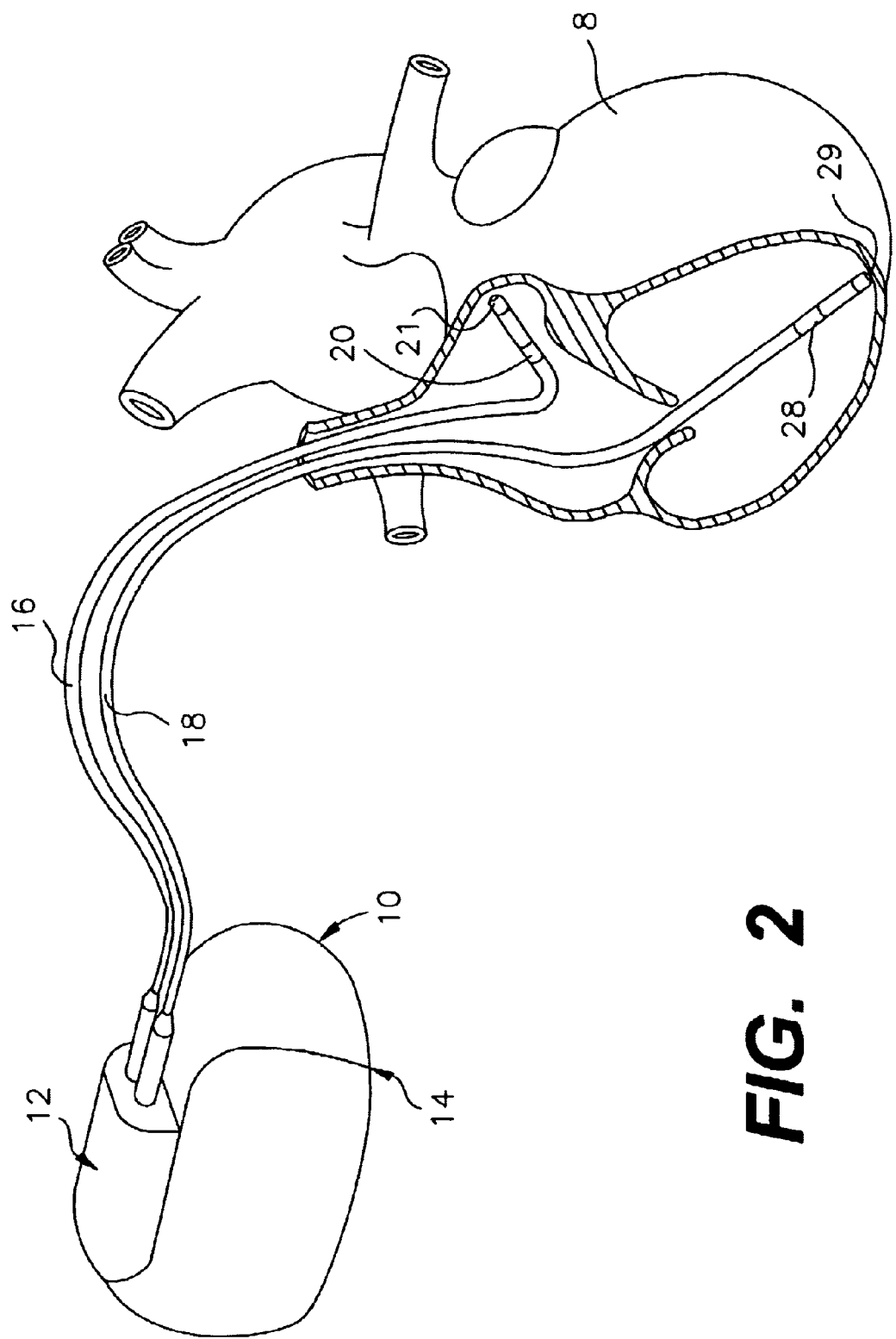
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. In one embodiment of the invention, one or both of atrial electrodes 20, 21 may serve as sensors to sense an atrial response (such as an atrial sensed response or an atrial pulse signal) in accordance with the present invention. Ventricular electrodes 28 and 29 at the distal end of ventricular pacing lead 18 are located in the right ventricle. One or both of ventricular electrodes 28, 29 may also serve to sense a ventricular response in accordance with the present invention.

Figure 3:
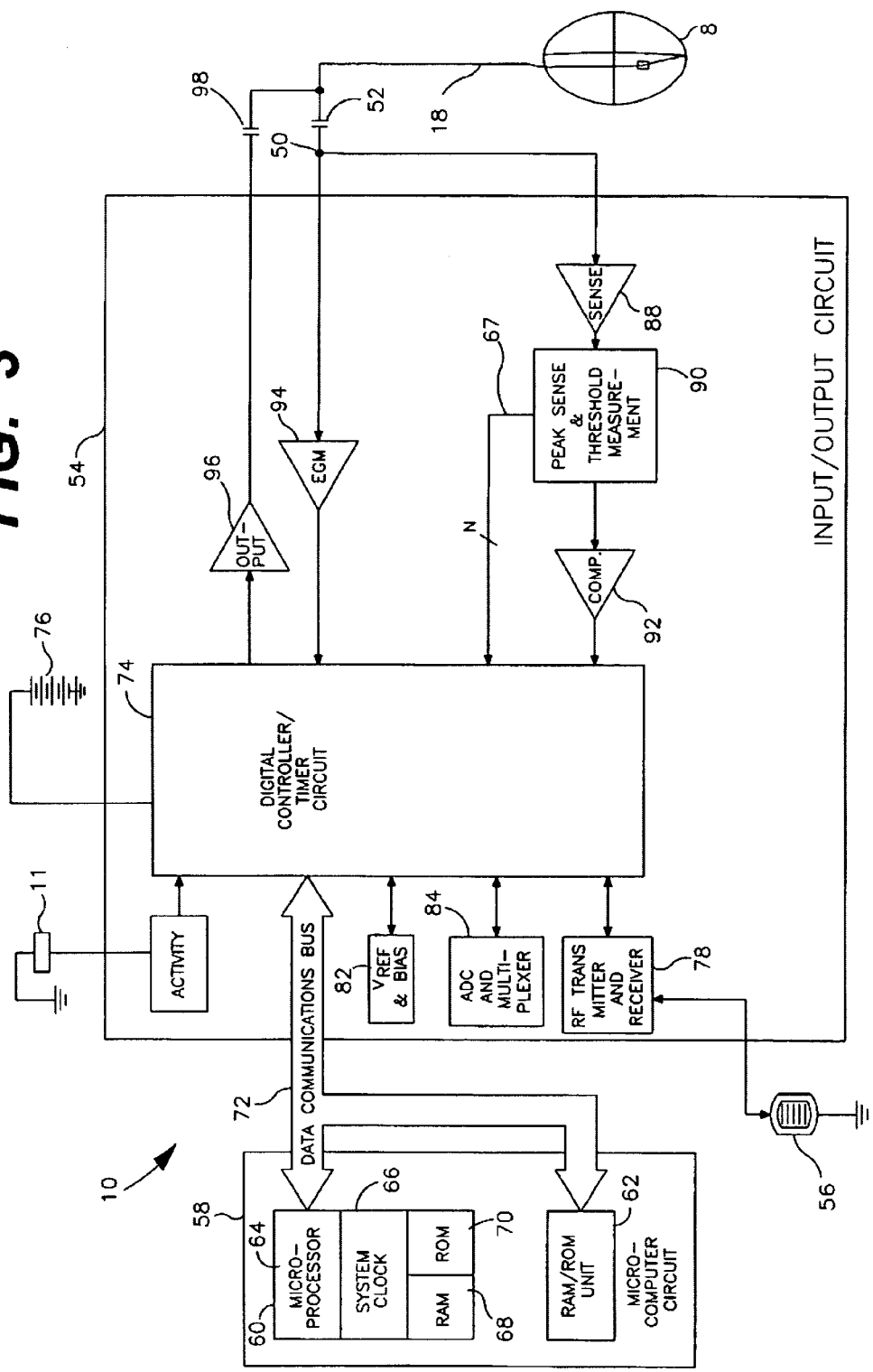
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16. In one embodiment of the invention, sensor 11 attached to lead 18 and an equivalent sensor attached to lead 16 may provide the two types of sensed information used in accordance with the present invention.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. Activity sensor 11 may also serve as a sensor in accordance with the present invention while an equivalent sensor attached to lead 16 (not shown) may serve as a second sensor in accordance with the present invention. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
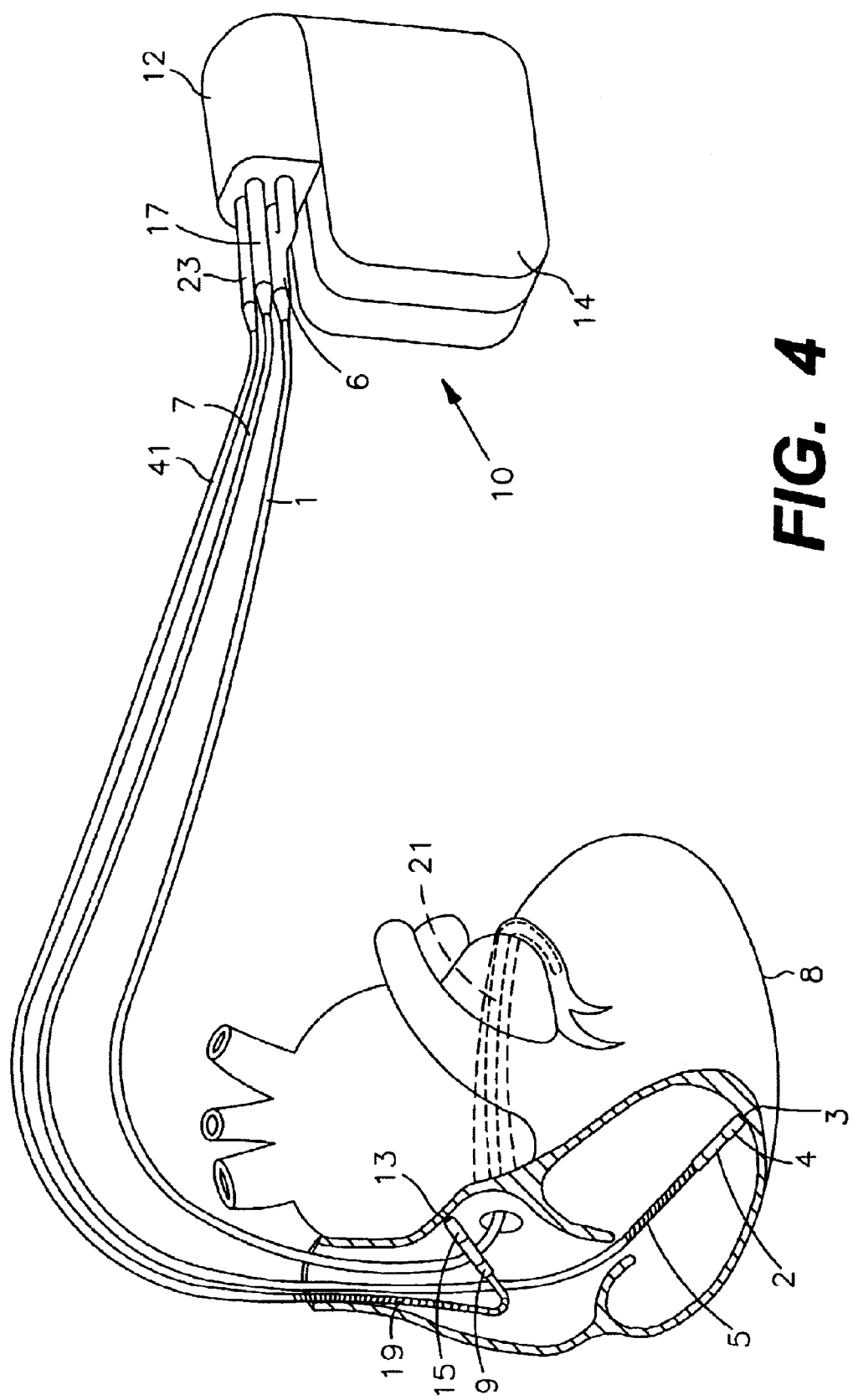
FIG. 4 is a schematic view of another embodiment of an implantable medical device, made in accordance with the present invention.
Figure 5:
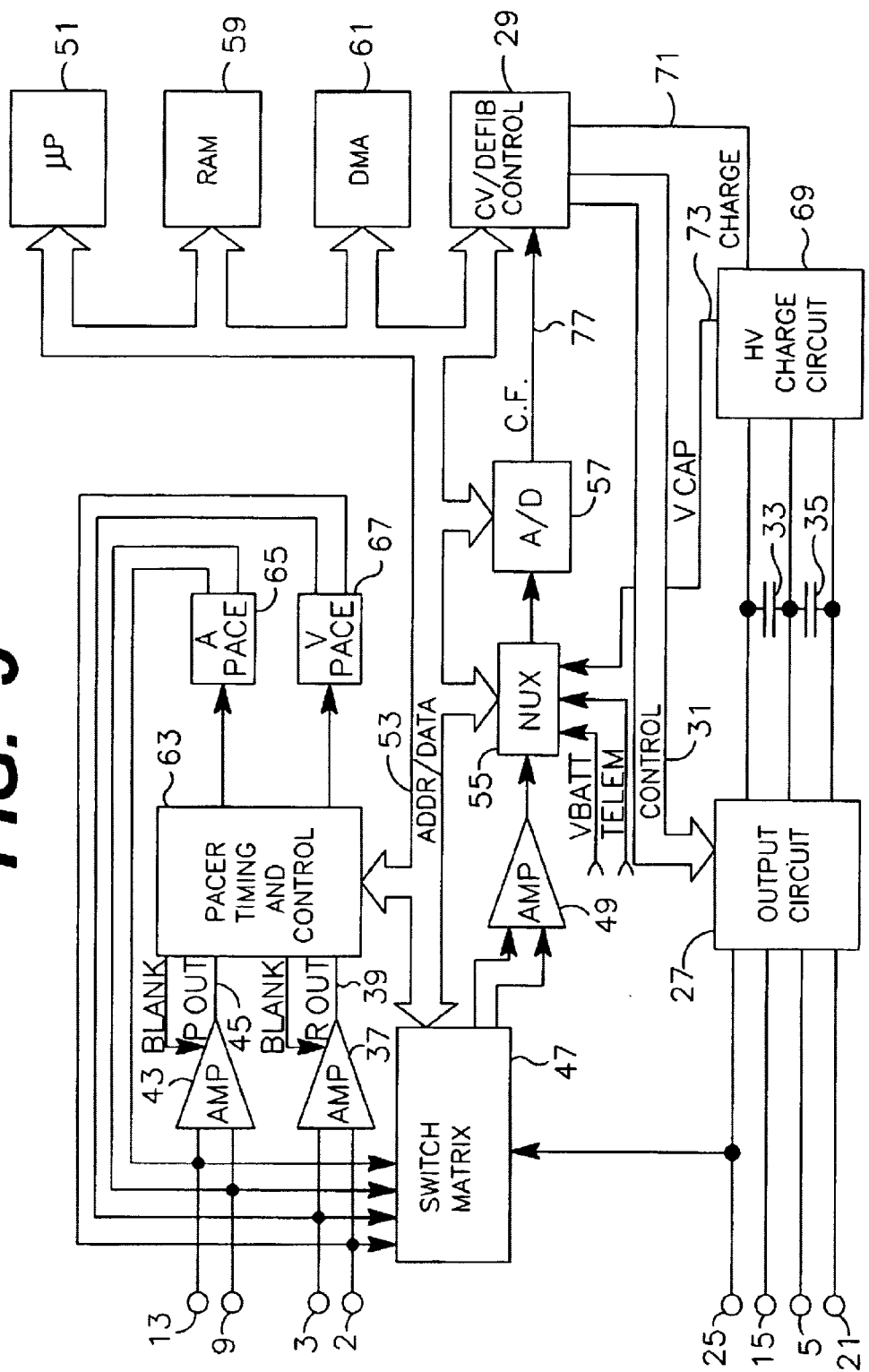
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 may be employed for cardiac pacing and for sensing ventricular depolarizations. One or both of electrodes 2, 3 may also serve to sense a ventricular response in accordance with the present invention. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 may be employed for atrial pacing and for sensing atrial depolarizations. One or both of electrodes 9, 13 may also serve to sense an atrial signal response in accordance with the present invention. Elongated coil electrode 19 is provided proximal to electrode 9 and coupled to the third conductor within lead body 7. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, VVI, DVI, VDD, AAI, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society* Press, pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Figure 6:
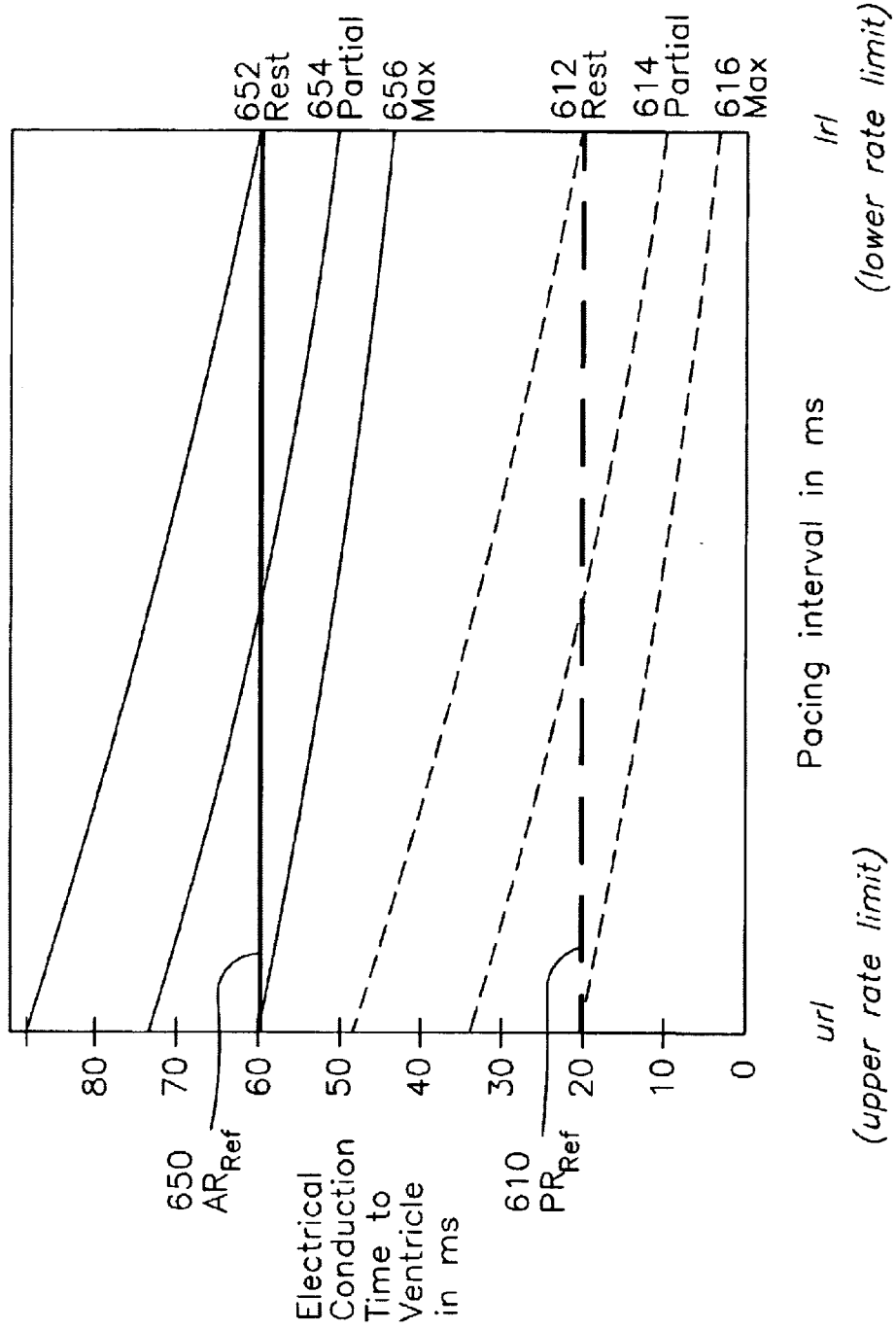
FIG. 6 is a graph illustrating atrial paced beats versus the pacing interval and atrial sensed beats versus the pacing interval for three different workload values, in accordance with the present invention.

FIG. 6 illustrates a graph of the variation of the AR interval (or AV interval) versus the pacing interval for three different workload values. A first reference line 610, shown as a dashed line, is superimposed over a first set of heart curves 612, 614 and 616. Reference line 610 provides a linear relationship between the pacing interval and the interval from a sensed atrial signal to a sensed ventricular signal (PR interval). A second reference line 650, shown as a solid line, is superimposed over a second set of heart curves 652, 654 and 656. Reference line 650 provides a linear relationship between the pacing interval and the interval from an atrial pacing pulse to a sensed ventricular signal (AR interval). Reference lines 610, 650, inter alia, may be used to link the pacing intervals with the sensed ventricular signal, i.e. with the measured electrical conduction time to the ventricle. Reference lines 610, 650 extend from zero workload at the lower rate limit, to maximum workload at the upper rate limit.

In the embodiment of FIG. 6, the curves associated with the PR intervals 612, 614 and 616 show lower electrical conduction time than curves associated with the AR intervals 652, 654, and 656. This is generally because, when the atrium is paced, there is some time delay from the pacing pulse to the actual activation of the atrial tissue. During spontaneous atrial response (e.g. normal atrial signals), it takes some time until the pacing device senses the atrial activation. This timing difference (AR interval versus PR interval) is essentially constant. Thus, as seen in FIG. 6, the AR and the PR intervals may have an offset with respect to each other that is relatively constant. In individual patients, either or both the AR and the PR intervals may be measured as a function of the heart rate or may be measured as sensor information. In one embodiment of the invention, the offset between the two intervals could be measured as a function of the heart rate. As a result, the heart curves for the PR interval are shown below the heart curves of the AR interval.

Both resting workload curves 612, 652 indicate a typical heart curve for a heart at rest. Curve 612 indicates the PR interval of a heart at rest and curve 652 indicates the AR interval of a heart at rest. Both partial workload curves 614, 654 indicate a typical heart curve for a heart working at partial (in this case 50%) workload capacity. Curve 614 indicates the PR interval of a heart working at partial workload capacity and curve 654 indicates the AR interval of a heart working at partial workload capacity. Both maximum workload curves 616, 656 indicate a typical heart curve for a heart working at maximum workload capacity. Curve 616 indicates the PR interval of a heart working at maximum workload capacity and curve 656 indicates the AR interval of a heart working at maximum workload capacity. On the reference line 610, the PR interval that corresponds with a certain pacing interval may serve as a reference value, $PR_{ref}$, against which curves 612, 614 and 616 may be compared. At each beat the PR interval may be measured and compared with the $PR_{ref}$ interval, which may be calculated as a function of the prevailing heart rate. In the embodiment of FIG. 6, the PR reference value is shown as a linear relationship. This linear relationship provides a constant slope or correlation between the change in pacing interval and the change in $PR_{ref}$. However, the reference line need not be linear, and, alternatively, optimum results can be obtained for a patient by adopting a non-linear reference curve with respect to the patient heartbeat curves. The pacing system of the present invention may respond with larger incremental steps at lower pacing rates, rather than at higher pacing rates. Such a response would yield a non-linear reference curve. Note that, even for a linear reference curve the slope may be positive (as shown), negative or zero. In cases in which the slope is zero, $PR_{ref}$ is a constant, and the pacing rate is changed in a direction to make the PR interval move toward $PR_{ref}$.

On the reference line 650, the AR interval that corresponds with a certain pacing interval may serve as a reference value, $AR_{ref}$, against which curves 652, 654 and 656 may be compared. At each beat the AR interval may be measured and compared with the $AR_{ref}$ interval, which may be calculated as a function of the prevailing heart rate. In the embodiment of FIG. 6, the AR reference value is shown as a linear relationship. This linear relationship provides a constant slope or correlation between the change in pacing interval and the change in $AR_{ref}$. However, the reference line need not be linear, and, alternatively, optimum results can be obtained for a patient by adopting a non-linear reference curve with respect to the patient heartbeat curves. The pacing system of the present invention may respond with larger incremental steps at lower pacing rates, rather than at higher pacing rates. Such a response would yield a non-linear reference curve. Note that, even for a linear reference curve the slope may be positive (as shown), negative or zero. In cases in which the slope is zero, $AR_{ref}$ is a constant, and the pacing rate is changed in a direction to make the AR interval move toward $AR_{ref}$.

Figure 7:
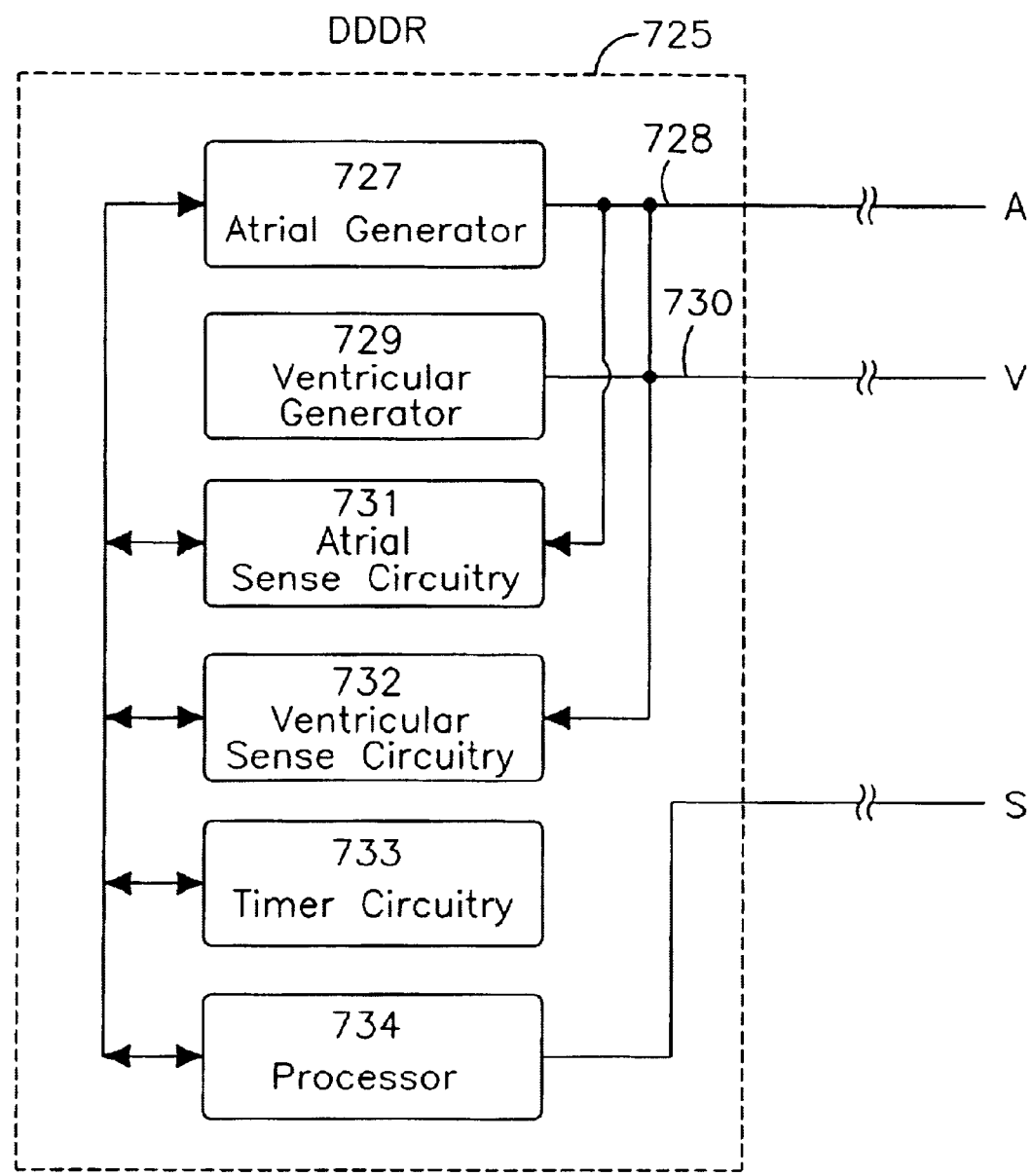
FIG. 7 is a block diagram illustrating components of one embodiment of a implantable pulse generating device in accordance with the present invention.
Figure 8:
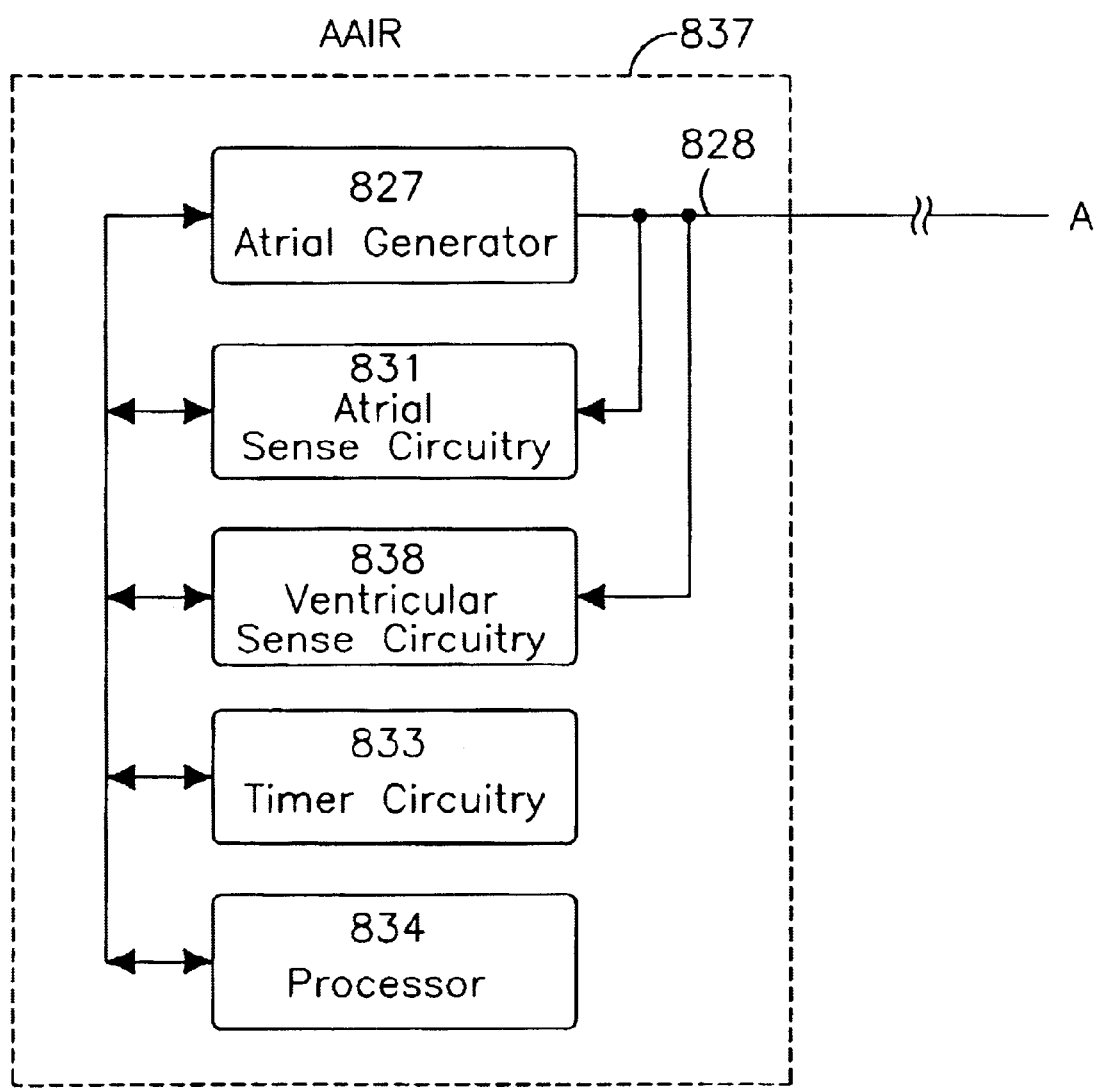
FIG. 8 is a block diagram illustrating components of another embodiment of an implantable pulse generating device in accordance with the present invention.

FIGS. 7 and 8 show block diagrams illustrative of DDDR and AAIR versions, respectively, of the present invention. The hardware and software elements represented by FIGS. 7 and 8 are well known in the art, as are the techniques of timing out intervals and microprocessor control of pacing functions.

In FIG. 7, there is illustrated one embodiment of an implantable pulse generating device in accordance with the present invention at 725. Device 725 may be, for example, a dual chamber pacer with atrial rate response to AR interval. Device 725 is connected to external lead 728, which has at least one electrode at about its distal tip adapted to be implanted in the patient's atrium A. Device 725 is also connected to external electrode 730, which has at least one electrode at about the distal tip thereof adapted to be implanted in the patient's ventricle V. As shown, atrial generator 727 may generate atrial stimulus signals, the output of which is connected to lead 728. Likewise, ventricular generator 729 may generated ventricular stimulus pulses, is connected to lead 730. Lead 728 may also be connected to atrial sense circuitry 731, while lead 730 may be connected to ventricular sense circuitry 732. Atrial sense circuitry 731 senses atrial heartbeats and may be used to operate the atrial channel in a demand mode. Likewise, ventricular sense circuitry 732 senses the occurrences of natural ventricular responses, or heartbeats, in a manner well-known in the art. Timer circuitry 733 is suitably used for timing out calculated atrial stimulating intervals, ventricular stimulating intervals, atrial-ventricular intervals and the like, in a well-known fashion. Timer circuitry 733 is shown controlled by logic such as that illustrated by processor 734. Timing signals are suitably generated under control of processor 734 to provide sense windows to control the sensing of the atrial and ventricular signals at circuits 731 and 732 respectively, in a well-known manner. Logic under the control of microprocessor 734 also controls the timing of delivery of atrial pulses from atrial generator 727 and ventricular pulses from ventricular generator 728.

In FIG. 8, there is shown another embodiment of an implantable pulse generating device in accordance with the present invention at 837. Implantable pulse generating device 837 may be an AAI pacer with atrial rate responsive to AR interval. It is to be understood that the system and method of this invention may be practiced using either unilateral or bilateral leads. A single chamber pacing system as illustrated at 837 may not include ventricular generator 828 or ventricular sense circuitry 832. However, the embodiment of FIG. 8 does include ventricular sense circuitry 838, adapted to sense the far field ventricular signal (i.e., an R wave) as discussed hereinabove. Ventricular sense circuitry 838 may in fact be the same sensing hardware as atrial sense circuitry 831, controlled by different window signals generated by timer circuitry 833 and processor 834. Ventricular sense circuitry 838 comprises conventional hardware having a time response adapted to the known morphology, amplitude and slew rate of the far field ventricular signal sensed by atrial lead 828.

Figure 9:
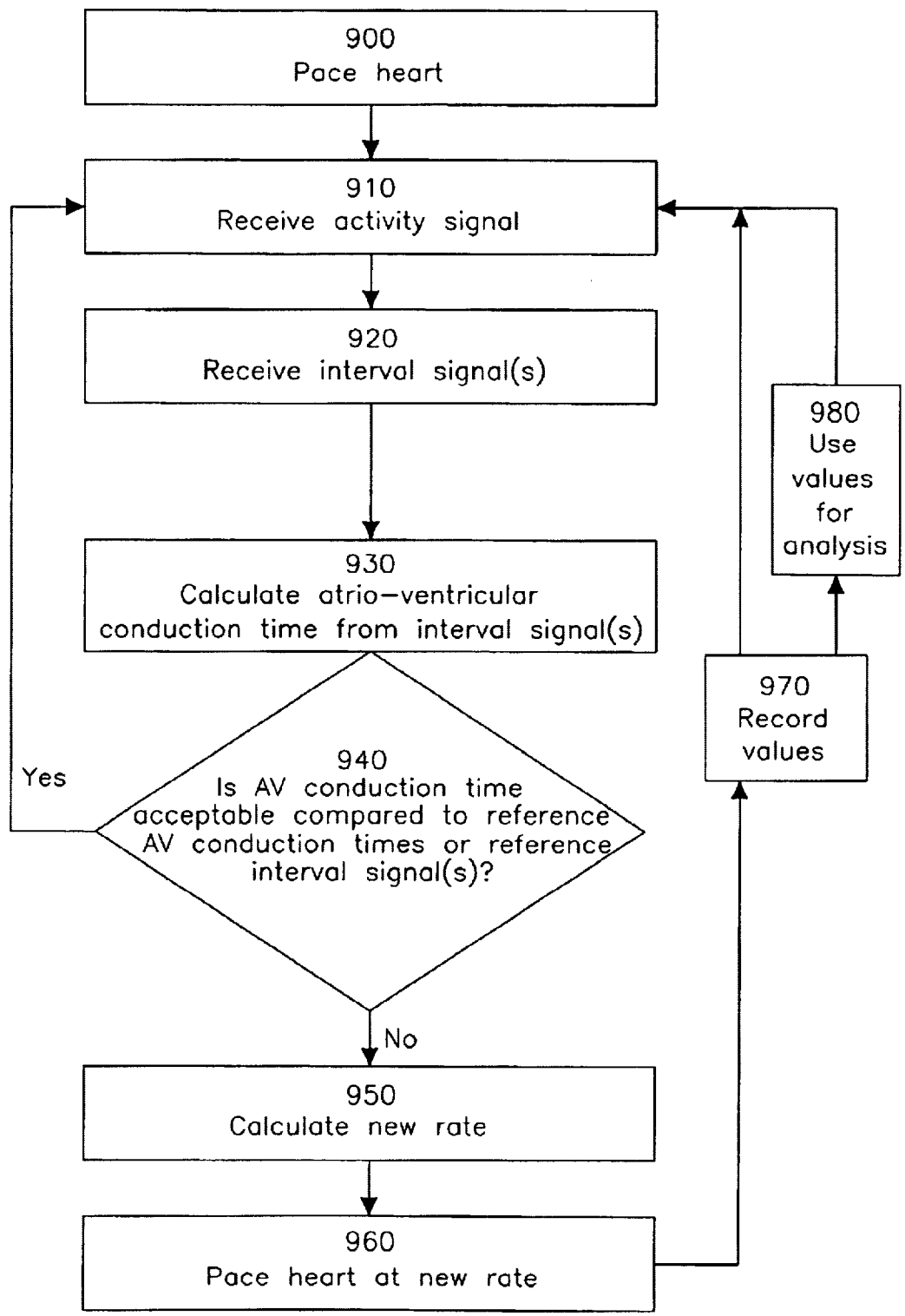
FIG. 9 is a flow diagram of one embodiment of a method for adapting the rate of stimulation in a cardiac pacing system in accordance with the present invention.

FIG. 9 shows a block diagram of a method for adapting the rate of a mammalian heart using an implantable medical device. Generally speaking, the method for reducing the rate of a mammalian heart by an implantable medical device comprises first pacing the mammalian heart at a predetermined heart rate. One or more interval signals may be received. An atrio-ventricular conduction time may then be calculated from the interval signals. Finally, the heart (pacing) rate may be adjusted based on the atrio-ventricular conduction time calculated from the interval signals. The heart (pacing) rate may also be adjusted based on the interval signals.

The method for adapting the rate of a mammalian heart may be performed by means of a computer algorithm program and/or software, which may be stored integral with, or remote from, IMD 10. Alternatively, the method may be performed in any other similar manner.

The computer algorithm program utilized in the present invention may be any program capable of being stored on an electronic medium, such as, for example, RAM 68 or ROM 70, and permitted to be accessed (and consequently run) by microprocessor 64. Alternatively, the method may be performed manually by a programmer electronically programming instructions to IMD 10, either remotely from a location away from IMD 10, or via an electronic connection with IMD 10.

Referring to FIG. 9, at Block 900, computer algorithm software operating on microprocessor 64 of IMD 10 paces heart 8 at a given rate. The pacing of heart 8 may occur by transmitting a plurality of stimulus pulses to heart 8 from microprocessor 64 to pacing and sensing leads 16, 18 via controller 74, as described above with reference to FIGS. 2 and 3.

At Block 910, computer algorithm software operating on microprocessor 64 of IMD 10 receives an activity response. As mentioned above with regards to FIG. 3, the activity response of heart 8 may be determined from heart rate signals received from the atrium and/or ventricle of heart 8 via sensing circuitry, including pacing and sensing lead 16, 18, EGM amplifier 94, sense amplifier 88, peak sense and threshold measurement unit 90 and comparator/threshold detector 92.

In one embodiment of the invention, this activity response is based on the activity level of the patient. The activity level may be determined using an activity sensor or any suitable means for sensing activity. The activity level of the patient may also be detected by detecting such indicators as the patient's heart rate, the temperature of the patient, etc. In one embodiment of the invention, activity sensor 11 is used to detect activity. Alternatively, an accelerometer may be used to detect activity. Alternatively, one or more additional sensors are used to detect activity level. Sensor circuitry may also be used to detect activity level. In one embodiment of the invention, the activity level determines the pacing rate (which may be the interval from an atrial event to the subsequent atrial pacing pulse.)

In one embodiment of the invention, activity may be indirectly determined based on input from one or more of the sensing lead sets described above. Sensing leads may be used measure the electrical activation of the heart, for example, the action potential, which causes the cells of the heart (and thus the heart itself) to contract. Thus, the time between the atrial beat and the subsequent ventricular beat may be indicative of the activity level of the patient.

Upon determining the activity level of the patient, at Block 920, computer algorithm software operating on microprocessor 64 of IMD 10 may then receive one or more interval signals. In one embodiment of the invention, the interval signal is from a paced atrial beat. Alternatively, the interval signal is from a sensed atrial beat. In another embodiment, the interval signal is a sensed ventricular signal. One or more of the interval signals may be used to cross-check the activity level.

At Block 930, the computer algorithm software may then calculate atrio-ventricular conduction time using one or more of the interval signals. In one embodiment of the invention, the atrio-ventricular conduction time may correspond to the time from a sensed atrial signal to a subsequent sensed ventricular signal (PR interval). Alternatively, the atrio-ventricular conduction time may also correspond to the time from an atrial pacing pulse to a subsequent sensed ventricular signal (AR interval). In the second instance, the atrial pacing pulse may be sent, for example, from IMD 10 to heart 8. Calculation of the atrio-ventricular conduction time may be accomplished using any suitable means.

At Block 940, computer algorithm software operating on microprocessor 64 of IMD 10 may then determine whether the atrio-ventricular conduction time is acceptable in comparison to a reference atrio-ventricular conduction time. This determination may be made using any suitable means. For example, computer algorithm software operating on microprocessor 64 may be used to compare the AV conduction time calculated at Block 930 with a database of reference AV conduction times. This database may be stored, for example in RAM 68 or ROM 70 of microcomputer circuit 58 of IMD 10. The reference AV conduction times may be dependent upon the age and health of the patient. If the AV conduction time calculated at Block 930 is suitable, computer algorithm software operating on microprocessor 64 of IMD 10 returns to Block 910, monitoring the activity level of heart 8.

Alternatively, the reference AV conduction times may be reference AR interval values and/or reference PR interval values. Thus, computer algorithm software operating on microprocessor 64 of IMD 10 may compare measured AR interval values to reference AR interval values to make the calculation indicated at Block 930. Alternatively, computer algorithm software operating on microprocessor 64 of IMD 10 may compare measured PR interval values to reference pR interval values to make the calculation indicated at Block 930.

If the AV conduction time calculated at Block 940 is determined to be unsuitable, computer algorithm software operating on microprocessor 64 of IMD 10, at Block 550, may calculate a new pacing rate for heart 8.

For example, in one embodiment of the invention, the measured PR interval may be compared to a $PR_{ref}$ value. If the measured PR interval is longer than the $PR_{ref}$ interval, the heart (pacing) rate may be too high and a lower pacing rate may be calculated. Alternatively, if the measured PR interval is shorter than the $PR_{ref}$ interval, the heart (pacing) rate may be too low and a higher pacing rate may be calculated.

In another embodiment of the invention, the measured AR interval may be compared to an $AR_{ref}$ value. If the measured AR interval is longer than the $AR_{ref}$ interval, the heart (pacing) rate may be too high and a lower pacing rate may be calculated. Alternatively, if the measured AR interval is shorter than the $AR_{ref}$ interval, the heart (pacing) rate may be too low and a higher pacing rate may be calculated.

Thus, in one embodiment of the invention, the measured AR interval may be used to determine a new pacing rate during atrial paced rhythm. Then a measured PR interval may be used to cross-check this pacing rate during intrinsic atrial rhythm. The difference between the AR and the PR interval may then be monitored continuously.

In another embodiment of the invention, both the measured AR interval and the measured PR interval may be compared to reference values to determine a new pacing rate. For example, the measured PR interval may be used to determine a new pacing rate. Then a measured AR interval may be used to cross-check this pacing rate.

At block 960, heart 8 may be paced at the new rate. As described above, the pacing of heart 8 may occur by transmitting a plurality of stimulus pulses to heart 8 from microprocessor 64 to pacing and sensing leads 16, 18 via controller 74, as described above with reference to FIGS. 2 and 3. In one embodiment of the invention, computer algorithm software adapts the pacing rate of heart 8 to a predetermined value. This predetermined value may be provided to computer algorithm from a database of heart rates. Alternatively, the pacing rate may be changed incrementally or in any suitable manner.

Upon reaching the new rate, computer algorithm software operating on microprocessor 64 of IMD 10 may then continue to pace heart 8 at the new rate. Pacing of heart 8, which may be done via the methods described above, at the new rate may also continue for a predetermined period of time.

At Block 970, computer algorithm software operating on microprocessor 64 of IMD 10 may record the values obtained during pacing. These values may be, for example, values obtained at Block 910 (i.e. activity level values), at Block 920 (i.e. interval values), at Block 930 (i.e. calculated atrio-ventricular conduction time values) and/or at Block 950 (i.e. pacing rate values). The recorded values may be stored in memory for future analysis as seen at Block 980. These values may be stored, for example in RAM 68 or ROM 70 of microcomputer circuit 58 of IMD 10. Upon storage of the values, the computer algorithm software may then return to Block 910 and continues to monitor the patient's activity level.

As seen at Block 980, computer algorithm software operating on microprocessor 64 of IMD 10 may also use the stored values for analysis before returning to Block 910 and continuing to monitor the patient's activity level. In one embodiment of the invention, analysis of the values may be made to determine reference AV conduction times to be used at Block 940. Alternatively, analysis of the values may be used to determine reference AR intervals and/or reference PR intervals to be used at Block 940. In another embodiment of the invention, analysis of the values may help determine acceptable activity levels to be used at Block 920.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for reducing the heart rate of a mammalian heart. The present invention is also not limited to the heart rate reduction methods, per se, but may find further application as a reducing means. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method for identifying and correcting an artificially increased pacing rate, comprising:

pacing at an increased pacing rate;

transmitting a pulse to cardiac tissue at a pacing rate;

receiving an activity signal;

receiving a first interval signal from an atrium;

receiving a second interval signal from a ventricle;

calculating atrio-ventricular conduction time from the first interval signal and the second interval signal;

comparing the atrio-ventricular conduction time to reference atrio-ventricular conduction times;

determining if the increased pacing rate is an artificially increased pacing rate;

calculating an adapted pacing rate if the increased pacing rate is the artificially increased pacing rate; and, pacing a heart at the adapted pacing rate to correct an artificially increased pacing rate.

2. The method of claim 1 further comprising:

re-adapting the pacing rate based on the second interval signal.

3. The method of claim 1 further comprising:

comparing the first interval signal to a first reference interval signal.

4. The method of claim 3 further comprising:

providing a database of first reference interval signals.

5. The method of claim 4 further comprising:

storing the first interval signal in the database of first reference interval signals.

6. The method of claim 1 further comprising:

comparing the second interval signal to a second reference interval signal.

7. The method of claim 6 further comprising:

providing a database of second reference interval signals.

8. The method of claim 7 further comprising;

storing the first interval signal in the database of first reference interval signals.

9. The method of claim 1 further comprising:

calculating an atrio-ventricular conduction time based on the first interval signal and the second interval signal.

10. The method of claim 9 further comprising:

adapting the pacing rate based on the atrio-ventricular conduction time.

11. The method of claim 10, further comprising: pacing the cardiac tissue at the adapted pacing rate.

12. The method of claim 9 further comprising:

comparing the atrio-ventricular conduction time with a reference atrio-ventricular conduction time.

13. The method of claim 1, further comprising:

pacing the cardiac tissue at the adapted pacing rate.

14. The method of claim 1, further comprising:

storing the atrio-ventricular conduction time.

15. A method for adapting a pacing rate that has been artificially increased to an inappropriately high rate, comprising:

means for pacing at an increased pacing rate;

means for transmitting a pulse to cardiac tissue at a pacing rate;

means for receiving an activity signal;

means for receiving a first interval signal from an atrium;

means for receiving a second interval signal from a ventricle;

means for calculating atrio-ventricular conduction time from the first interval signal and the second interval signal;

means for comparing the atrio-ventricular conduction time to reference atrio-ventricular conduction times;

means for determining if the increased pacing rate is an artificially increased pacing rate;

means for calculating an adapted pacing rate if the increased pacing rate is the artificially increased pacing rate; and, means for pacing a heart at the adapted pacing rate to correct an artificially increased pacing rate.

* * * * *